(12) United States Patent
Parthasaradhi Reddy et al.

(10) Patent No.: US 7,638,634 B2
(45) Date of Patent: Dec. 29, 2009

(54) AMORPHOUS ESOMEPRAZOLE HYDRATE

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN)

(73) Assignee: Hetero Drugs Limited (IN)

( * ) Notice: Subject to any disclaimer, the term of this patent is extended or adjusted under 35 U.S.C. 154(b) by 0 days.

(21) Appl. No.: 12/399,514

(22) Filed: Mar. 6, 2009

(65) Prior Publication Data

US 2009/0198066 A1    Aug. 6, 2009

Related U.S. Application Data

(62) Division of application No. 11/570,473, filed as application No. PCT/IN2005/000197 on Jun. 15, 2005, now Pat. No. 7,563,812.

(51) Int. Cl.
*C07D 401/12* (2006.01)
(52) U.S. Cl. .................................... 546/273.7
(58) Field of Classification Search ............... 546/273.7
See application file for complete search history.

(56) References Cited

U.S. PATENT DOCUMENTS 4,738,974 A    4/1988 Briindstrom
5,714,504 A    2/1998 Lindberg et al.
5,877,192 A    3/1999 Lindberg
6,369,085 B1   4/2002 Cotton et al.

FOREIGN PATENT DOCUMENTS

| EP | 0005129 A1 | 3/1979 |
|----|------------|--------|
| EP | 0005129 B1 | 3/1979 |
| WO | 27988 A1 | 5/1993 |
| WO | 9828294 A1 | 7/1998 |
| WO | 2004002982 A2 | 1/2004 |
| WO | 2004020436 A1 | 3/2004 |
| WO | 2004076440 A1 | 3/2004 |

OTHER PUBLICATIONS

PCT Notification of Transmittal of the International Search Report and the Written Opinion of the International Searching Authority, or the Declaration Dated Jun. 15, 2005.

*Primary Examiner*—Patricia L Morris
(74) *Attorney, Agent, or Firm*—Caesar, Rivise, Bernstein, Cohen & Pokotilow, Ltd.

(57) ABSTRACT

The present invention relates to a novel amorphous form of esomeprazole hydrate, to a process for its preparation and to a pharmaceutical composition containing it. Thus, tetrahydrofuran and water are added to esomeprazole potassium salt at 25-30° C., cooled to 20° C. and then the pH is adjusted to 7.5-8.0 with acetic acid. The reaction mass is cooled to 5° C., stirred for 2 to 3 hours at 0-5° C., filtered the mass, washed with chilled mixture of water and tetrahydrofuran (2:1) and again washed with water. The wet cake is dried at 30-35° C. under vacuum to reach the moisture content to 25-30%. The solid is again dried in rotovapour at 25-30° C. under nitrogen atmosphere to give amorphous esomeprazole hydrate.

7 Claims, 1 Drawing Sheet

AMORPHOUS ESOMEPRAZOLE HYDRATE

This specification is a Divisional of U.S. application Ser. No. 11/570,473 filed Dec. 12, 2006, now U.S. Pat. No. 7,563,812 which is a National Stage Entry of PCT/IN2005/000197, filed Jun. 15, 2005.

FIELD OF THE INVENTION

The present invention relates to a novel amorphous form of esomeprazole hydrate, to a process for its preparation and to a pharmaceutical composition containing it.

BACKGROUND OF THE INVENTION

Omeprazole, chemically 5-methoxy-2-[[(4-methoxy-3,5-dimethyl-2-pyridinyl)methyl]sulfinyl]-1H-benzimidazole and its therapeutic uses are disclosed in European Patent No. 5129. Omeprazole is a well-known gastric acid secretion inhibitor, and is useful as an anti ulcer agent. Omeprazole has a stereogenic center at sulfur and therefore exist as two optical isomers such as R-omeprazole and S-omeprazole (esomeprazole).

The salts of the enantiomers of omeprazole are described in WO 94/27988. PCT Publication No. WO 98/28294 disclosed esomeprazole in an amorphous form, a partly crystalline form A, and a substantially crystalline form B.

PCT Publication No. WO 2004/076440 A1 described crystalline forms, Form I and Form II, of esomeprazole, and its hydrates. PCT Publication No. WO 2004/020436 A1 described amorphous hydrates of esomeprazole magnesium and process for their preparation. PCT Publication No. WO 2004/002982 A2 described amorphous form esomeprazole free base and process for its preparation.

U.S. Pat. No. 6,369,085 described crystalline forms of esomeprazole magnesium, esomeprazole magnesium dihydrate, esomeprazole magnesium trihydrate and esomeprazole potassium.

The alkaline salts of (S)-enantiomer of omeprazole (esomeprazole), the pharmaceutical preparations of these salts and the method of treatment of gastric acid-related diseases using them are disclosed in U.S. Pat. No. 4,738,974, U.S. Pat. No. 5,877,192 and U.S. Pat. No. 5,714,504.

We have discovered a stable novel amorphous form of esomeprazole hydrate. The novel amorphous esomeprazole hydrate is stable over the time and has good flow properties and so, the novel amorphous hydrate is suitable for formulating esomeprazole.

The object of the present invention is to provide a stable novel amorphous form of esomeprazole hydrate, process for preparing it and pharmaceutical composition containing it.

DETAILED DESCRIPTION OF THE INVENTION

In accordance with the present invention, there is provided a novel amorphous form of esomeprazole hydrate. The water content of the amorphous form of esomeprazole hydrate is between 3.0 and 5.0% by weight of amorphous form of esomeprazole hydrate, typically between 3.5 and 4.5% by weight of amorphous form of esomeprazole hydrate.

The amorphous form of esomeprazole hydrate, designated as amorphous esomeprazole hydrate, is characterized by having broad X-ray diffraction spectrum as shown in FIG. 1.

According to one aspect of the present invention, a process is provided for the preparation of amorphous esomeprazole hydrate, which comprises:

a) providing a solution of esomeprazole in the mixture of water and a solvent or a mixture of solvents selected from tetrahydrofuran, acetonitrile, 1,4-dioxane and dimethyl formamide; and b) precipitating amorphous esomeprazole hydrate from the solution.

The solution of esomeprazole may be prepared by dissolving esomeprazole in a mixture of water and the solvent or by dissolving esomeprazole in the solvent and then adding water to the solution.

The solution of esomeprazole may also be prepared by adding an acid to a salt of esomeprazole in the presence of water and the solvent to obtain a solution of esomeprazole.

During precipitation the ratio of water to the solvent is maintained at 0.5:1 to 4:1 by volume, preferably at 1:1 to 3:1 by volume and more preferably at 1.5:1 to 2.5:1 by volume.

The precipitation of amorphous esomeprazole hydrate may be carried out by conventional methods such as cooling, seeding, partial removal of solvent, addition of extra quantity of water or a combination thereof.

The precipitated amorphous esomeprazole hydrate may be collected by filtration or centrifugation and then dried.

The drying may preferably carried out at about 20-35° C. in rotovapour.

The amorphous esomeprazole hydrate is novel and forms part of the invention. Amorphous esomeprazole hydrate may be used in pharmaceutical preparations.

Amorphous esomeprazole hydrate is useful intermediate for preparing amorphous or crystalline anhydrous esomeprazole.

Amorphous esomeprazole hydrate may, for example, be converted to amorphous esomeprazole by slurring with an insoluble solvent.

Esomeprazole hydrate may also be useful intermediate for preparation of known pharmaceutically acceptable salts by conventional means.

The above process may be used to purify crude esomeprazole or a crude esomeprazole salt by providing a solution of crude esomeprazole and precipitating pure esomeprazole hydrate as described above. The pure amorphous esomeprazole hydrate obtained is optionally converted to anhydrous esomeprazole by a method such as slurrying in an organic solvent and filtering to obtain anhydrous esomeprazole.

Crude esomeprazole refers to esomeprazole for which further treatment is required to get esomeprazole of desired purity (pure esomeprazole).

According to another aspect of the present invention there is provided a pharmaceutical composition comprising amorphous esomeprazole hydrate and a pharmaceutically acceptable carrier. Preferable pharmaceutical composition is a solid oral dosage form.

Figure 1:
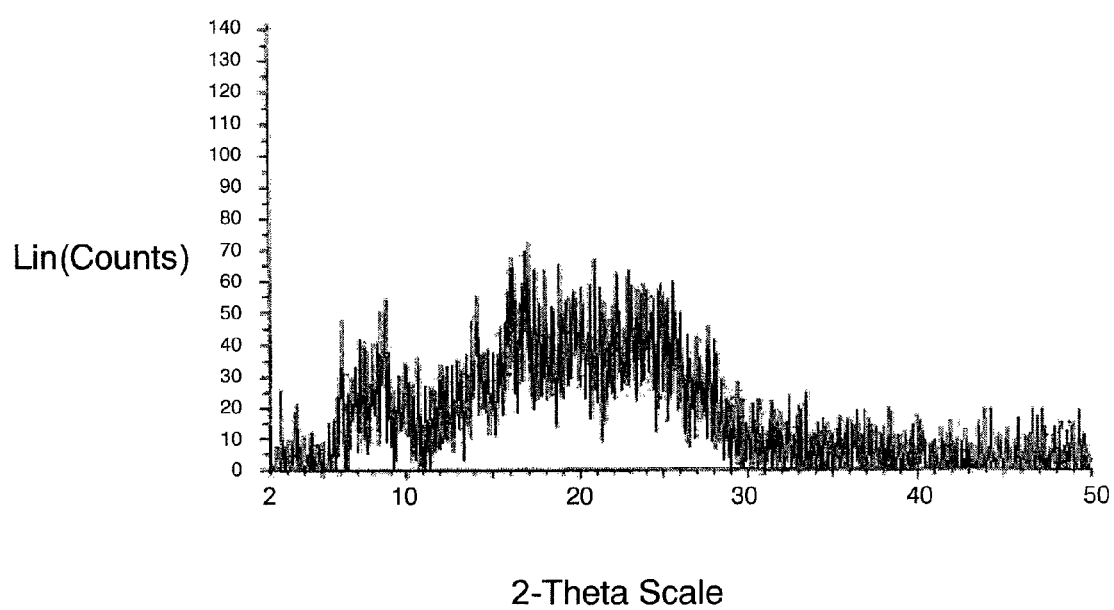
FIG. 1 is an X-ray powder diffraction pattern of amorphous esomeprazole hydrate.

X-Ray powder diffraction spectrum was measured on a Bruker axs D8 advance x-ray powder diffractometer having a Copper-K$\alpha$ radiation. Approximately 1 gm of sample was gently flattened on a sample holder and scanned from 2 to 50 degrees two-theta, at 0.03 degrees two-theta per step and a step time of 0.5 seconds. The sample was simply placed on the sample holder. The sample was rotated at 30 rpm at a voltage 40 KV and current 35 mA.

The following examples are given for the purpose of illustrating the present invention and should not be considered as limitations on the scope or spirit of the invention.

EXAMPLE 1

Tetrahydrofuran (250 ml) and water (500 ml) are added to esomeprazole potassium salt (50 gm) at 25-30° C., cooled to 20° C. and then the pH is adjusted to 7.5-8.0 with acetic acid. The reaction mass is cooled to 5° C., stirred for 2 to 3 hours at 0-5° C., filtered the mass, washed with 50 ml of chilled mixture of water and tetrahydrofuran (2:1) and again washed with water (100 ml). The wet cake is dried at 30-35° C. under vacuum to reach the moisture content to 25-30%. The solid is again dried in rotovapour at 25-30° C. under nitrogen atmosphere to give 26.3 gm of amorphous esomeprazole hydrate (HPLC Purity: 99.92%, Moisture Content: 4.0%).

EXAMPLE 2

Acetonitrile (250 ml) and water (700 ml) are added to esomeprazole potassium salt (50 gm) at 25-30° C., cooled to 20° C. and then the pH is adjusted to 7.5-8.0 with acetic acid. The reaction mass is cooled to 5° C., stirred for 2 to 3 hours at 0-5° C., filtered the mass, washed with 50 ml of chilled mixture of water and acetonitrile (3:1) and again washed with water (100 ml). The wet cake is dried at 30-35° C. to reach the moisture content to 30-35%. The solid is again dried in rotovapour at 25-30° C. under nitrogen atmosphere to give 26.1 gm of amorphous esomeprazole hydrate (HPLC Purity: 99.91%, Moisture Content: 4.1%).

We claim:

1. A process for preparation of amorphous esomeprazole hydrate of which comprises:
    a) providing a solution of esomeprazole in the mixture of water; and a solvent or mixture of solvents selected from tetrahydrofuran, acetonitrile, 1,4-dioxane and dimethylformamide; and
    b) precipitating amorphous esomeprazole hydrate from the solution.

2. The process as claimed in claim 1, wherein the ratio of water to the solvent during precipitation is maintained at 0.5:1 to 4:1 by volume.

3. The process as claimed in claim 2, wherein the ratio of water to the solvent during precipitation is maintained at 1:1 to 3:1 by volume.

4. The process as claimed in claim 3, wherein the ratio of water to the solvent during precipitation is maintained at 1.5:1 to 2.5:1 by volume.

5. The process as claimed in claim 1, wherein the precipitation of amorphous esomeprazole hydrate is carried out by cooling, seeding, partial removal of solvent, addition of extra quantity of water or a combination thereof.

6. The process as claimed in claim 5, further comprises the precipitated amorphous esomeprazole hydrate is collected by filtration or centrifugation and then dried.

7. The process as claimed in claim 6, wherein the drying is carried out at about 20-35° C. in rotovapour.

* * * * *